(12) United States Patent
Margalit et al.

(10) Patent No.: US 8,144,973 B2
(45) Date of Patent: Mar. 27, 2012

(54) MULTI-MODAL IMAGING

(75) Inventors: Tamir Margalit, Mazor (IL); Ram Oron, Nes Ziona (IL); Amir Noy, Kfar Mordehai (IL)

(73) Assignee: Orbotech Ltd., Yavne (IL)

( * ) Notice: Subject to any disclaimer, the term of this patent is extended or adjusted under 35 U.S.C. 154(b) by 458 days.

(21) Appl. No.: 12/409,788

(22) Filed: Mar. 24, 2009

(65) Prior Publication Data

US 2010/0245813 A1   Sep. 30, 2010

(51) Int. Cl.
*G06K 9/00*   (2006.01)

(52) U.S. Cl. .................. 382/147; 356/237.1; 356/237.6; 382/144; 382/149; 382/150

(58) Field of Classification Search .......... 382/144–147, 382/149, 150; 356/237.1–237.6
See application file for complete search history.

(56) References Cited

U.S. PATENT DOCUMENTS

| | | | |
|---|---|---|---|
| 4,692,943 A * | 9/1987 | Pietzsch et al. ............... 382/148 |
| 5,227,839 A | 7/1993 | Allen |
| 5,298,977 A | 3/1994 | Shintani et al. |
| 5,495,337 A * | 2/1996 | Goshorn et al. ............. 356/601 |
| 5,517,234 A | 5/1996 | Gerber et al. |
| 5,784,484 A | 7/1998 | Umezawa |
| 5,969,372 A | 10/1999 | Stavely et al. |
| 5,990,468 A | 11/1999 | Cornuejols |
| 5,991,055 A | 11/1999 | Haselby et al. |
| 6,031,931 A | 2/2000 | Chiu et al. |
| 6,208,750 B1 | 3/2001 | Tsadka |
| 6,433,561 B1 | 8/2002 | Satya et al. |
| 6,781,687 B2 | 8/2004 | Fisch et al. |
| 6,832,843 B2 | 12/2004 | Adler et al. |
| 7,015,445 B2 | 3/2006 | Bishop |
| 7,039,228 B1 | 5/2006 | Pattikonda et al. |
| 7,130,036 B1 | 10/2006 | Kuhlmann et al. |
| 7,231,080 B2 | 6/2007 | Hakim et al. |
| 7,355,689 B2 | 4/2008 | Almogy et al. |
| 7,397,552 B2 | 7/2008 | Guetta et al. |
| 2002/0093650 A1 | 7/2002 | Zemer et al. |
| 2002/0186878 A1 | 12/2002 | Hoon et al. |
| 2005/0122510 A1 | 6/2005 | Levin et al. |
| 2007/0058164 A1 | 3/2007 | Shibata et al. |
| 2008/0186556 A1 | 8/2008 | Almogy et al. |

* cited by examiner

*Primary Examiner* — Gregory J Toatley
*Assistant Examiner* — Iyabo S Alli
(74) *Attorney, Agent, or Firm* — Sughrue Mion, PLLC

(57) ABSTRACT

A method for scanning a surface with a number of different illumination configurations, the method comprises capturing a plurality of images in a sequential manner during a single sweep, each image including one or more lines of pixels, sequentially altering an illumination configuration used to capture the plurality of images according to a predefined sequence of illumination configurations and shifts of the relative position of the imaging unit for capturing each of the plurality of images, and repeating the sequence of illumination configurations settings and associated image capture positions until a desired area of the surface is scanned, wherein said predefined shift is between 10 pixels and less then one pixel.

40 Claims, 6 Drawing Sheets

MULTI-MODAL IMAGING

FIELD OF THE INVENTION

The present invention relates to Automated Optical Inspection (AOI) systems for inspection of electrical circuits and more particularly to image acquisition of Printed Circuit Boards (PCB) in AOI systems.

BACKGROUND OF THE INVENTION

Automated optical inspection (AOI) systems are typically employed in the inspection of electrical circuits, including Printed Circuit Boards (PCBs), flat panel displays, chip carriers, integrated circuits and the like. Some known AOI systems operate based on a single illumination configuration that is typically configured for detecting specific types of defects. Other known AOI system operate using a plurality of illumination configurations to allow detection of a wider range of defects.

Commercially available AOI systems include the Inspire™ 9060 using color images, Discovery™ and V-300™ systems for inspecting bare PCBs, the Trion™ system for inspecting populated PCBs, FPI-6090™ and FPI-7590™ systems for inspecting flat display panels, and ICP 8060™ system for inspecting chip carriers. All of the above systems were or are commercially available from Orbotech Ltd. of Yavne, Israel.

U.S. Pat. No. 7,397,552 entitled "Optical inspection with alternating configurations", the contents of which is incorporated herein by reference, describes an imaging system for inspection of a wafer including an illumination module providing pulsed optical radiation and a mechanical scanner arranged to scan an area of the surface irradiated by the illumination module and to irradiate a plurality of successive, substantially overlapping frames on the surface by respective successive pulses of the pulsed radiation, each said successive frame having an overlap with a respective preceding frame of at least 50%. The imaging system includes a system controller, arranged to vary a configuration of the imaging system in alternation between a first configuration and a second, different, configuration, whereby the sequence of images comprises at least a first set of images captured in the first optical configuration and a second set of images captured in the second optical configuration. The imaging system includes an image processor, arranged to jointly process the first image and the second image to detect a defect in the sample by analyzing features on the surface as imaged using each of the first and the second optical configurations.

U.S. Pat. No. 6,781,687 entitled "Illumination and Image Acquisition System" assigned to Orbotech Ltd., the contents of which is incorporated herein by reference, describes an inspection system that illuminates a surface of an electrical circuit with flashes of light. The flashed light is from at least two spectrally different sources temporally spaced. Each flash is incident on the surface at the same location and generally the same angle of incidence. A camera forms a separate optical image from each flash of light. The images formed with the different flashes are combined to form a full view image. Analysis of the full view image is performed to determine defects in the electric circuit.

US Patent Application Publication No. US2002/0186878 entitled "System and Method for Multiple Image Analysis", the contents of which is incorporated herein by reference, describes a system for analyzing multiple images to locate defects in a test component. The system includes first and second light sources each emitting a different color light from a different angle and a camera with a processor to generate two or more images. The images are used to construct a 3-dimensional image of the object and are then analyzed to determine whether a dimension of the test component is acceptable.

The Amethyst™ system commercially available by Orbotech Ltd. of Yavne, Israel provides for sequentially acquiring several images of an area with different illumination as described in http://www.orbotech.com/D2_ProductsGroup.asp?MenuID=566 (Nov. 16, 2008).

SUMMARY OF THE INVENTION

An aspect of some embodiments of the invention is the provision of a system and method for scanning a surface to be optically inspected with a plurality of images of different areas of the surface and with a plurality of illumination configurations during a single sweep.

An aspect of some embodiments of the present invention is the provision of a method for scanning a surface with a number of different illumination configurations, the method comprising: capturing a plurality of images in a sequential manner during a single sweep, each image including one or more lines of pixels; sequentially altering an illumination configuration used to capture the plurality of images according to a predefined sequence of illumination configurations and shifts of the relative position of the imaging unit for capturing each of the plurality of images; and repeating the sequence of illumination configurations settings and associated image capture positions until a desired area of the surface is scanned, wherein said predefined shift is between 10 pixels and less then one pixel.

Optionally, images captured over one sequence partially overlap.

Optionally, each image covers 100 lines of pixels or less.

Optionally, each image covers 1 line of pixels.

Optionally, the relative motion is provided with a shift error of less than one pixel.

Optionally, the method comprises acquiring at least two sets of images in a single sweep using at least two different illumination configurations and constructing an area image from each set so as to obtain at least two area images.

Optionally, the at least two area images cover a substantially same portion of the surface, wherein the substantially same portion is substantially larger than a portion of the surface covered in a single image.

Optionally, substantially larger is at least 100 times larger.

Optionally, substantially larger is at least 1000 times larger.

Optionally, the at least two area images are automatically registered with an alignment error of less than one pixel.

Optionally, the method comprises inspecting the area images, wherein the inspecting includes comparing the area images without registering the area images.

Optionally, the method comprises adjusting spatial alignment between the area images based on the pre-defined shift.

Optionally, the method comprises computing registration between one of the area images and a master image and registering the other area image of the at least two area images with the master image using the computed registration.

Optionally, the images are captured with at least one camera selected from a group including: a line camera and a multi-line camera.

Optionally, the illumination configuration is switched on and off or flashed during image capturing.

Optionally, the illumination configurations of the sequence differ in one or more parameters selected from a group including: wavelength, intensity, angle, angular distribution, polarization, and fluorescence.

Optionally, the illumination configuration setting is altered at a frequency greater than the mechanical frequency of a scanning unit scanning the surface.

An aspect of some embodiments of the present invention is the provision of an automatic optical inspection system capable of scanning a surface with a number of different illumination configurations comprising an imaging unit comprising at least one camera and at least one illumination unit, wherein the at least one illumination unit is configured for providing illumination in each of the different illumination configurations and wherein the at least one camera is configured for capturing a series of images over one sweep, each image of the sequence including one or more lines of pixels; a scanning unit configured for providing translation between the surface and the imaging unit at a resolution in the order of magnitude of one pixel or less; and a controller configured for activating each of the different illumination configurations based on a pre-defined sequence and repeating the sequence for the duration of the sweep and for activating the camera to capture an image during each illumination activation.

Optionally, images captured over the pre-defined sequence partially overlap.

Optionally, the scanning unit is configured for providing translation in the order of magnitude of one pixel or less between capturing of each of the images in the series.

Optionally, the scanning unit provides a translational shift between each image capture that corresponds to a number of pixel lines captured by one image divided by the number of different illumination configurations in the sequence.

Optionally, each image covers 100 lines of pixels or less.

Optionally, each image covers one line of pixels.

Optionally, the error in the translation shift between each image captured corresponds to an error of less than one pixel.

Optionally, the at least one camera is selected from a group including: a line camera and a multi-line camera.

Optionally, the imaging unit comprises a plurality of image sensors aligned side by side to cover a full width of the panel.

Optionally, the system comprises an analyzer configured for constructing at least two area images from at least two sets of images captured in a single sweep, each set captured with a different illumination configuration.

Optionally, the at least two area images cover a substantially same portion of the surface, wherein the substantially same portion is substantially larger than a portion of the surface covered in a single image.

Optionally, substantially larger is at least 100 times larger.

Optionally, substantially larger is at least 1000 times larger.

Optionally, the spatial alignment error between the at least two area images is less than one pixel.

Optionally, the at least two area images are automatically aligned with an alignment error of less than one pixel.

Optionally, the analyzer is configured for comparing the area images without registering the area images.

Optionally, the analyzer is configured for adjusting a spatial alignment between the area images based on a pre-defined translation shift between images captured with the different illumination configuration.

Optionally, the analyzer is configured for computing registration between one of the area images and a master image and for registering another area image from the at least two area images with the master image using the registration computed.

Optionally, the illumination configuration setting is altered at least at a frequency of 1 KHz.

Optionally, the illumination configuration setting is altered at a frequency greater than the mechanical frequency of the automatic optical inspection system.

Optionally, the at least one illumination unit includes at least one LED configured for illuminating a portion of the surface to be imaged.

Optionally, the at least one illumination unit includes illumination with strobe capability.

Optionally, the different illumination configurations differ in one or more parameters selected from a group including: wavelength, intensity, angle, angular distribution, polarization, and fluorescence.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
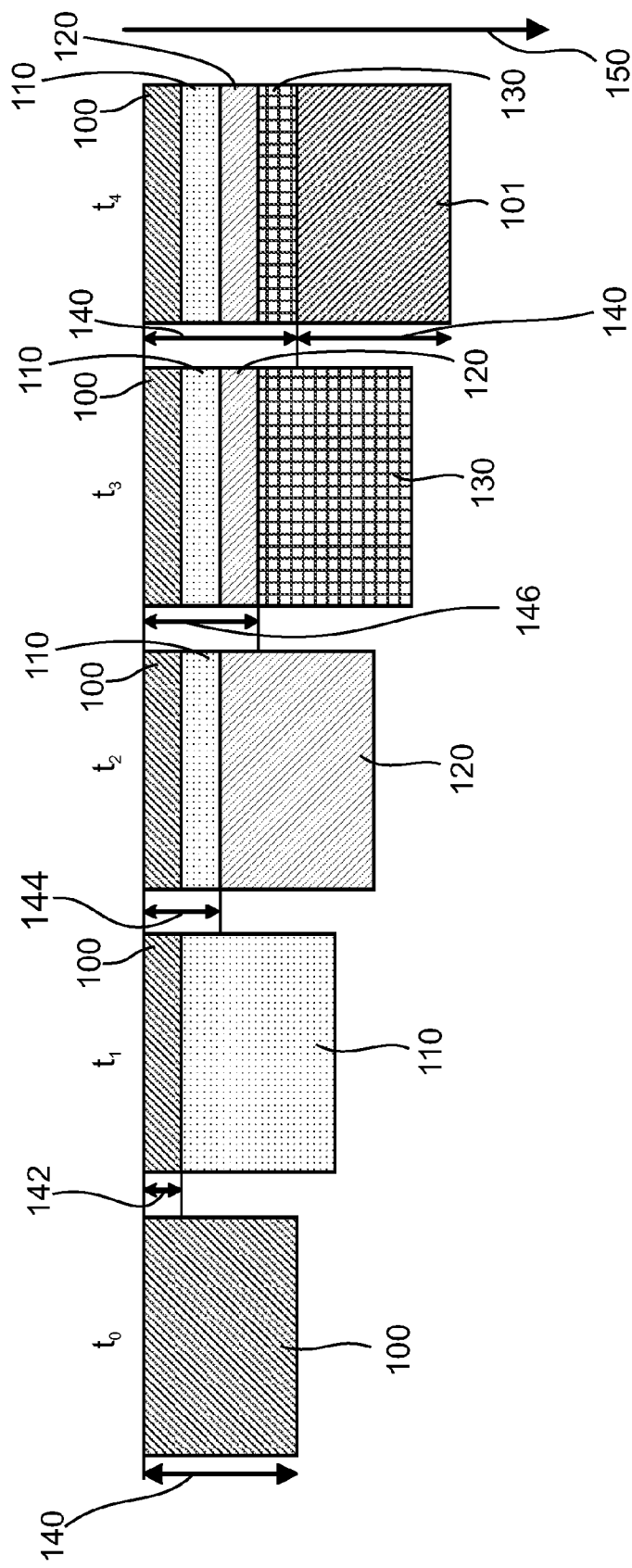
FIG. 1 shows a simplified schematic diagram of areas of an object imaged with a multi-line or area camera during relative motion between the camera and the object using a sequence of four different illumination configurations in accordance with some embodiments of the present invention.

The present invention relates to Automated Optical Inspection (AOI) systems for inspection of electrical circuits and more particularly to image acquisition of Printed Circuit Boards (PCB) in AOI systems.

An aspect of some embodiments of the present invention is the provision of an image acquisition system that captures a sequence of images of a given width of an object to be inspected using different illumination configurations in a pre-defined order and/or sequence that is typically cyclically repeated during relative motion between the object and an imaging unit, e.g. camera, over a single sweep. According to some exemplary embodiments, the illumination sequence is coordinated with relative motion, e.g. translation between the object and the camera. According to some exemplary embodiments, each illumination is activated, e.g. switched on and off or flashed, at a frequency corresponding to defined shifts in position of the object with respect to the camera. Typically the shift is between about 10 pixels and less than the width of a pixel. In some embodiments the shift is a pixel or a fraction of a width of a pixel, so that overlap exists between images captured with different illumination configurations. In some exemplary embodiments, the shift is as high as 50 pixels.

According to some embodiments of the present invention, the pre-defined order of illumination configurations is repeated throughout the scanning procedure. In some exemplary embodiment the pre-defined order includes a plurality of different sequences of illumination. In some exemplary embodiments, the sequence is selected to match a nature of a pattern being inspected, e.g. multiple dense conductors and heat sinks, and is altered based on the nature of the pattern in a specified areas. Typically, the imaging unit includes one or more imagers and/or image sensors such as a Charged Coupled Device (CCD), a Complimentary Metal Oxide Semiconductor (CMOS) or another suitable sensor and one or more illumination sources, e.g. one or more illumination sources for each camera. The imaging unit may include a line camera, a multi-line camera or an area camera. As used herein, a line camera captures one line of pixels and a multi-line camera captures several (typically 2-100) lines of pixels. An area camera captures more than 100 lines at one time. Typically, the ratio between the number of pixels along a length and width of an area camera is closer to one than the ratio between the number of pixels along a length and width of a multi-line camera and/or a line camera. In some embodiments of the invention the length of the lines is large enough to capture the entire object being imaged. In others side by side scans, with possible overlap, are used to capture the entire object.

According to embodiments of the present invention, illumination from each illumination configuration is switched on and off or flashed in sequence toward the object for imaging at defined intervals during relative motion between the object and the camera. In some exemplary embodiments, the illumination sequence is cyclically repeated until a sweep of the image acquisition system is completed. The different illumination configuration may differ for example, in intensity, angular distribution, fluorescence, polarization or color, (e.g. wavelength).

In some embodiments of the invention, the relative motion is continuous. In others the motion is stepped and imaging takes place between steps.

For cameras capturing one line of pixels at a time, the shift may correspond to a fraction of a pixel. In some exemplary embodiments, if N illumination configurations are used, the shift corresponds to the width of 1/N of a pixel width. For example, the shift may correspond to a width of a half a pixel when two illumination configurations are used, a width of one third a pixel when three illumination configurations are used, or a width of one quarter a pixel when four illumination configurations are used. In some exemplary embodiments, if N illumination configurations are used, the shift corresponds to the width of 1/N of the line, or the plurality of lines captured by the camera. It is noted that the above shifts may not be exact fractions, smaller or larger shifts may be implemented to obtain super-sampling or sub-sampling respectively.

According to some embodiments of the present invention, the inspection system has a translation accuracy corresponding to a fraction of a pixel, e.g. 1-20% of a pixel width, corresponding to an accuracy of approximately ±0.1-5 microns.

In some exemplary embodiments of the present invention, the shifts in a sequence of illumination configurations are not necessarily uniform and smaller or greater shifts are defined for different illumination configurations. For example, for a sequence including two illumination configurations, a shift after switching on or flashing the first illumination configuration may correspond to a width of 0.4 of a pixel and a shift after switching on or flashing the second illumination configuration may correspond to a width of 0.6 of a pixel, so that together there is a shift of 1 pixel and the end of the sequence.

In some embodiments of the invention, the shifts are smaller than or larger than 1/N of a pixel. When smaller than 1/N, there is overlap between images with the same illumination configuration.

According to some embodiments of the present invention, the illumination includes strobe ability so that the different illumination configurations can be flashed at a high frequency, e.g. 1-1000 KHz during scanning. In some exemplary embodiments, the invention includes high frequency switching (on and off) of continuous illumination. In some exemplary embodiments, Light Emitting Diode (LED) illumination is used. Exemplary LEDs may include K2 LEDs available by Luxeon and high power LEDs available by Roithner Lasertechnik. In some exemplary embodiments illumination units such as are described in US Patent Application Publication No. 2008-0089052, entitled "Linear Light Concentrator" assigned to Orbotech Ltd. the contents of which is incorporated herein by reference are used to provide for one or more illumination configurations. Typically, one image is captured per flash and a series of flashes are provided to capture a series of images from each of the different illumination configurations and for each area of the object scanned.

An aspect of some embodiments of the present invention is the provision of a method for constructing a plurality of area images including an area that is substantially larger than the area of a single exposure of a camera, each area image resulting from multiple exposures with a single illumination configuration from a sequence of illumination configurations that is cyclically repeated during relative motion between the object and a camera during a single sweep. Typically, the size of the area images is pre-defined and common to all illumination configurations in the sequence so that an area image is constructed for each of the illumination configurations after a pre-defined number of cycles. According to some embodiments of the present invention, shift or translation between the different area images constructed over the pre-defined number of cycles (each area image captured with a different illumination configuration of the sequence) is small and/or negligible, e.g. in the order of magnitude of one to ten pixels or less than a pixel, so that different sequential area images with different illumination configurations provide for capturing substantially a same area with a plurality of different illumination configurations. In some exemplary embodiments, each area image covers a portion of an area inspected over a single sweep. In some exemplary embodiments, each area image is an image of the area imaged during a single sweep. In some exemplary embodiments, for objects scanned over a plurality of sweeps, the area image is an image of the entire inspected object, e.g. scanned over a plurality of sweeps.

According to embodiments of the present invention, for an area image constructed from M images captured during a single sweep, the illumination configuration is switched at least N*M times for N number of illumination configurations. In some exemplary embodiments, a plurality of images, in an order of magnitude of approximately up to 300,000 for line cameras are used to construct a single area image of an object to be inspected over a single sweep. In some exemplary embodiments, the object is scanned with around 2 to 4 different illumination configurations so that for line cameras the illumination configuration is switched approximately 1,000,000 times. According to some embodiments of the present invention, for a pixel size of approximately 20 microns, for a switching frequency of 20-40 KHz and/or assuming a scanning velocity of 200 mm/sec, the illumination configuration is switched every 5-10 microns. Typically, for line cameras, the distance covered between flashes of the same illumination configuration corresponds to the width of one pixel (or less), e.g. the width of a line (or less).

The inventors have found that the alignment, e.g. accurate sub-pixel alignment, between area images captured with different illumination configurations provide for comparing between area images captured with different illumination configurations without requiring calculating registration between the area images captured with different illumination configurations, e.g. calculating registration by image analysis. Typically, the cumulative shift error between the area images captured with different illumination configurations is in the order of magnitude of approximately one pixel or less. According to some embodiments of the present invention, inspection is provided based on design rule inspection, where inspection is provided by analysis of a constructed area image based on a set of rules or other method, such as die to die, template matching or auto correlation. According to some embodiments of the present invention, area images of substantially a same area constructed from different illumination configurations are compared for inspection without performing registration between the images constructed from different illumination configurations. According to some embodiments of the present invention, area images of substantially a same area constructed from different illumination configurations are compared for inspection without registering the images with a master. According to some embodiments of the present invention, inspection is performed without requiring registration of the area images to each other and/or to a master image, e.g. reference image.

According to some embodiments of the present invention, registration is computed between an area image captured with one of the illumination configuration in a sequence and a reference image. Typically the reference image is a master and/or template image that includes a full area to be inspected. According to some embodiments of the present invention, the reference image is an image that is stored in the system's memory, e.g. a CAD drawing, a CAM drawing or a template image. In some embodiments system's memory may include external memory accessible by the system, e.g. disk-on-key, network disk drives.

According to some embodiments of the present invention, the computed registration is repeated for registration of corresponding area images captured with other illumination configurations. According to some embodiments of the present invention, the registration computed for one of the illumination configurations is adjusted when applied to each of the other illumination configurations based on a known shift and/or translation between consecutive images captured with the different illumination configurations in the sequence. In some embodiments of the invention, the shift is small enough so that the position difference between images taken with different illuminations can be ignored in analyzing the images for anomalies. The inventors have found that registration computation need not be repeated, e.g. with or without adjustment, for the different illumination configurations due to the small and accurate shift, e.g. sub-pixel shift error, and/or translation between each of the images captured and that registration between the different area images is not required.

According to some embodiments of the present invention, high frequency switching, e.g. 1-50 KHz between the different illumination and/or small spatial shifts between the camera and surface, e.g. smaller than 100 microns, provide for shift errors that are small and/or negligible.

The inventors have found that although a plurality of area images, e.g. full view images each captured with a different illumination configuration, can be constructed by first capturing a full scanned image during a first sweep with a first illumination configuration and then repeatedly scanning the object during subsequent sweeps with different illumination configurations, such a process would be less efficient than the system and methods described herein. For example, the time required for multiple sweeps of an object is typically longer than the time required for capturing a plurality of images with different illumination configurations during a single sweep. In addition, performing multiple sweeps to obtain a plurality of or area images each captured with a different illumination configuration would require that registration be repeated for each full view and/or area image obtained in a sweep. Repeated registration typically requires more processing time and power as compared to performing registration once for images captured with one illumination configuration repeating the registration for images captured with other illumination configurations as is suggested by embodiments of the present invention.

Furthermore, illumination configurations that would typically not allow registration may be used with the system and methods described herein. For example, registration may be performed on one of the illumination configurations conducive to registration and that registration may be copied for the illumination configuration that is not conducive to registration. For example, registration of shiny applications may be relatively easy with a strong bright field illumination, but may be more difficult with a high dark field and low bright field illumination. Although systems using full color images do not require registration for the different colors, usage of color images typically increases cost and complexity of the system as compared to monochrome based systems. In addition the optical performance may be degraded due to usage of color images.

It is noted that any one of the illumination configurations in the series may be selected to compute the registration between an area image and the reference image so that the illumination configuration most suitable for calculation of registration in a particular area can be selected. In some exemplary embodiments, one or more area images may be combined to obtain an area image including a plurality of illumination configuration, e.g. a full colored image.

Reference is now made to FIG. 1 showing a simplified schematic diagram of areas of a panel imaged with a multi-line camera during relative motion between a camera and the panel using a sequence of four different illumination configurations in accordance with embodiments of the present invention. According to some embodiments of the present invention, at time slot $t_0$ the camera captures an image, e.g. an image frame, of an exposed area 100 of the panel using one illumination configuration. Typically, area 100 includes a plurality of lines of pixels, e.g. 1-50 lines. Between time slot $t_0$ and subsequent time slot $t_1$, the camera moves relative to the panel by a distance equal to a fraction of the length of exposed area 100, e.g. one quarter of a length 140 of exposed area 100, and a second image of a second exposed area 110 is captured at time slot $t_1$. According to some embodiments of the present invention, second exposed area 110 is imaged using a second illumination configuration, e.g. different from the first illumination configuration. Exposed areas 100 and 110 partially overlap, e.g. with a shift of length 142 between them in the scanning direction 150 e.g. a shift equivalent to one quarter of length of exposed area 100.

Between time slot $t_1$ and subsequent time slot $t_2$, the camera moves relative to the panel by a distance equal to a fraction of the length of exposed area 100, e.g. one quarter of a length 140 of exposed area 100, and a third exposed area 120 is imaged at time slot $t_2$. According to some embodiments of the present invention, exposed area 120 is captured using a third illumination configuration, e.g. different from the first and second illumination configuration. Exposed areas 100 and 120 partially overlap with a shift of length 144 between them, e.g. overlap equivalent to one half the length of exposed area 100.

Between time slot $t_2$ and subsequent time slot $t_3$, the camera moves relative to the panel by a distance equal to a fraction of the length of exposed area 100, e.g. one quarter of a length 140 of exposed area 100 and a fourth exposed area 130 is imaged at time slot $t_3$. According to some embodiments of the present invention, exposed area 130 is captured using a fourth illumination configuration, e.g. different from the first, second, and third illumination configuration. Exposed area 100 and 130 partially overlap with a shift of length 146 between them in this example equivalent to three quarters of the length of exposed area 100. Between time slot $t_3$ and subsequent time slot $t_4$, the camera moves relative to the panel by a distance equal to a fraction of the length of exposed area 100, e.g. one quarter of length 140 and a fifth image 101 is captured at time slot $t_4$. Typically, the exposed area for each of the images captured is the same. In some exemplary embodiments, the exposed area may vary for some of the illumination configurations and overlap may exist between subsequent images taken with a same illumination configuration.

In some exemplary embodiments, two or more lines of pixels are captured in each image and the shift between capturing of images with different illumination configurations are a fraction of the number of lines captured in each image. For example if two lines of pixels are captured in each image and four different illumination configurations are used in sequence, the shift between image capture may be ½ pixel width. In another example, if four lines of pixels are captured in each image and four different illumination configurations are used in sequence, the shift between image capture may be 1 pixel width. In some embodiments, the shift between images is less than a pixel (or at most several pixels) even when a relatively large number of lines are imaged at one time.

According to some embodiments of the present invention, the process is repeated and a subsequent image is captured of a new exposed area 101 using the first illumination configuration. Typically, the sequence is repeated until the desired area of the panel is scanned. In some exemplary embodiments, exposed area 100 and 101 are shifted by length 140 so that exposed area 101 begins where exposed area 100 ends. In some exemplary embodiments, exposed areas 100 and 101 partially overlap so as to obtain super-sampling. In some exemplary embodiments, there is a gap between exposed areas 100 and 101 so as to obtain sub-sampling. Typically, an area image is constructed from a plurality of captured image frames captured with the same illumination configuration, based on a pre-defined shift between image frames e.g. shift between areas 100 and 101. Typically, registration is not required for constructing the area image. In some exemplary embodiments, the pre-defined shift provides for super sampling and registration is performed between sequential image frames captured with the same illumination configuration, e.g. images of areas 100 and 101. In some exemplary embodiments, computed registration from one illumination configuration can be used to register images captured with other illumination configurations in the sequence.

According to some embodiments of the present invention, registration is performed between a constructed area image captured with the same illumination configuration, e.g. a series of images including the exposed areas 100 and 101, and a reference image, a reference full view image of the area of the panel being scanned. According to some embodiments of the present invention, computed registration based on one of the illumination configurations can be used for registration of the area images obtained with the other illumination configuration, so their comparison to the reference is not required for each of the illumination configuration. In some embodiments of the invention, the shift is small enough so that the position difference between images taken with different illuminations can be ignored in analyzing the images for anomalies.

Although, embodiments of the invention have been described herein above where the camera moves, e.g. translates relative to the panel, it is noted that in some exemplary embodiments of the present invention, the panel moves, e.g. translates relative to the camera and/or both the camera and panel move relative to each other.

Although embodiments of the invention have been described herein above as using a sequence of four different illumination configurations, it is noted that a different number of illumination configurations may be used, e.g. more or fewer than four different illumination configurations.

According to some embodiments of the present invention, the different illumination configurations may differ in one or more properties, e.g. color (wavelength), intensity, angular distribution, and polarization. Examples of pairs of illumination configurations that my be used to image an object may include UV and red illumination, high intensity and low intensity illumination, blue and red illumination, UV and blue illumination, UV and white illumination, red and white illumination, small angle (bright field) and large or grazing angle (dark field) illumination. In some exemplary embodiments, a separate light source is used for each of the different illumination configurations. In some exemplary embodiments, one light source provides for two or more illumination configurations. In some exemplary embodiments, a plurality of light sources is used to provide for a single illumination configuration.

Figure 2A:
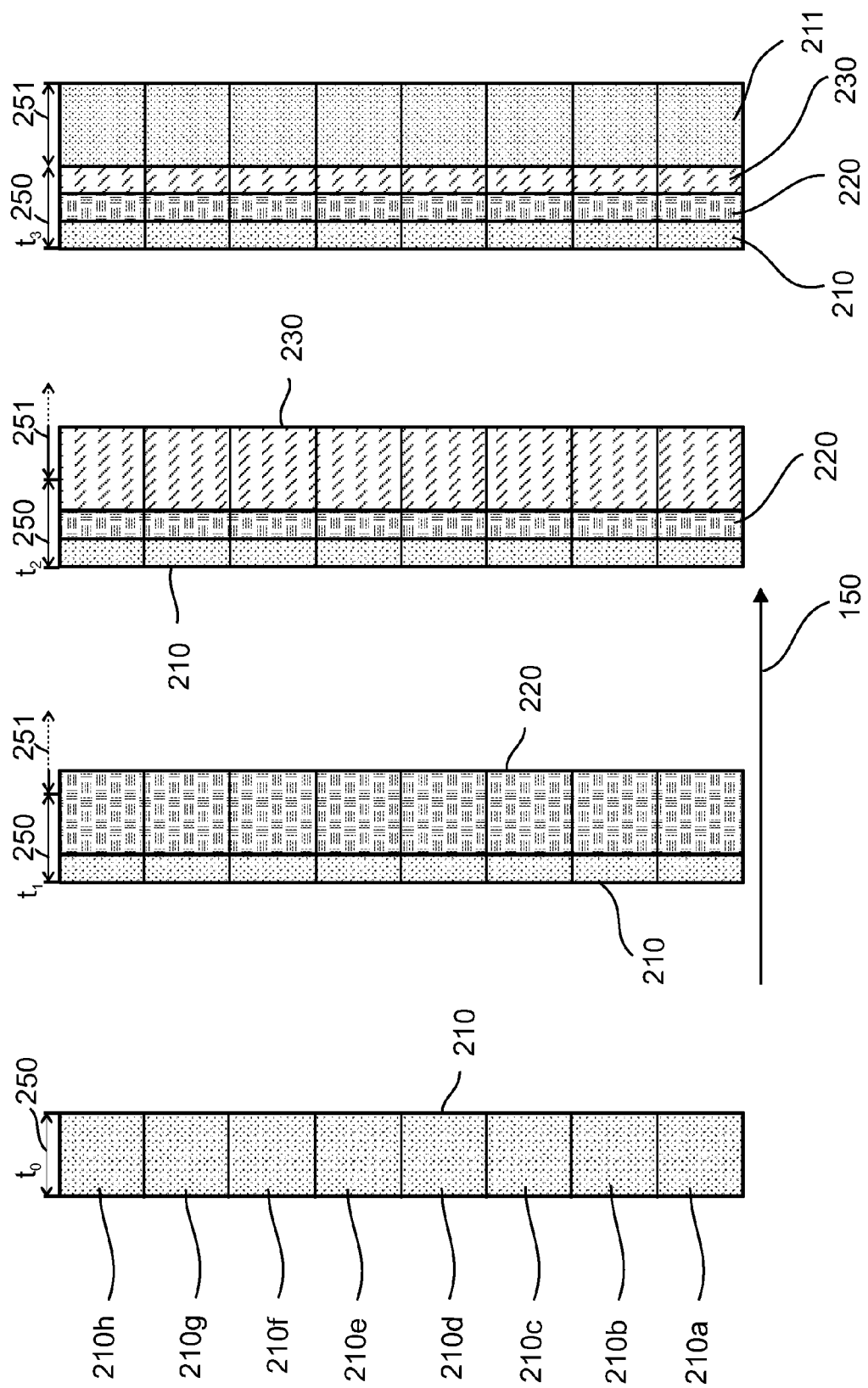
FIGS. 2A and 2B show two simplified schematic diagrams of line images produced by a line camera using a sequence of three different illumination configurations each image shifted by a fraction of a pixel width in accordance with some embodiments of the present invention.
Figure 2B:
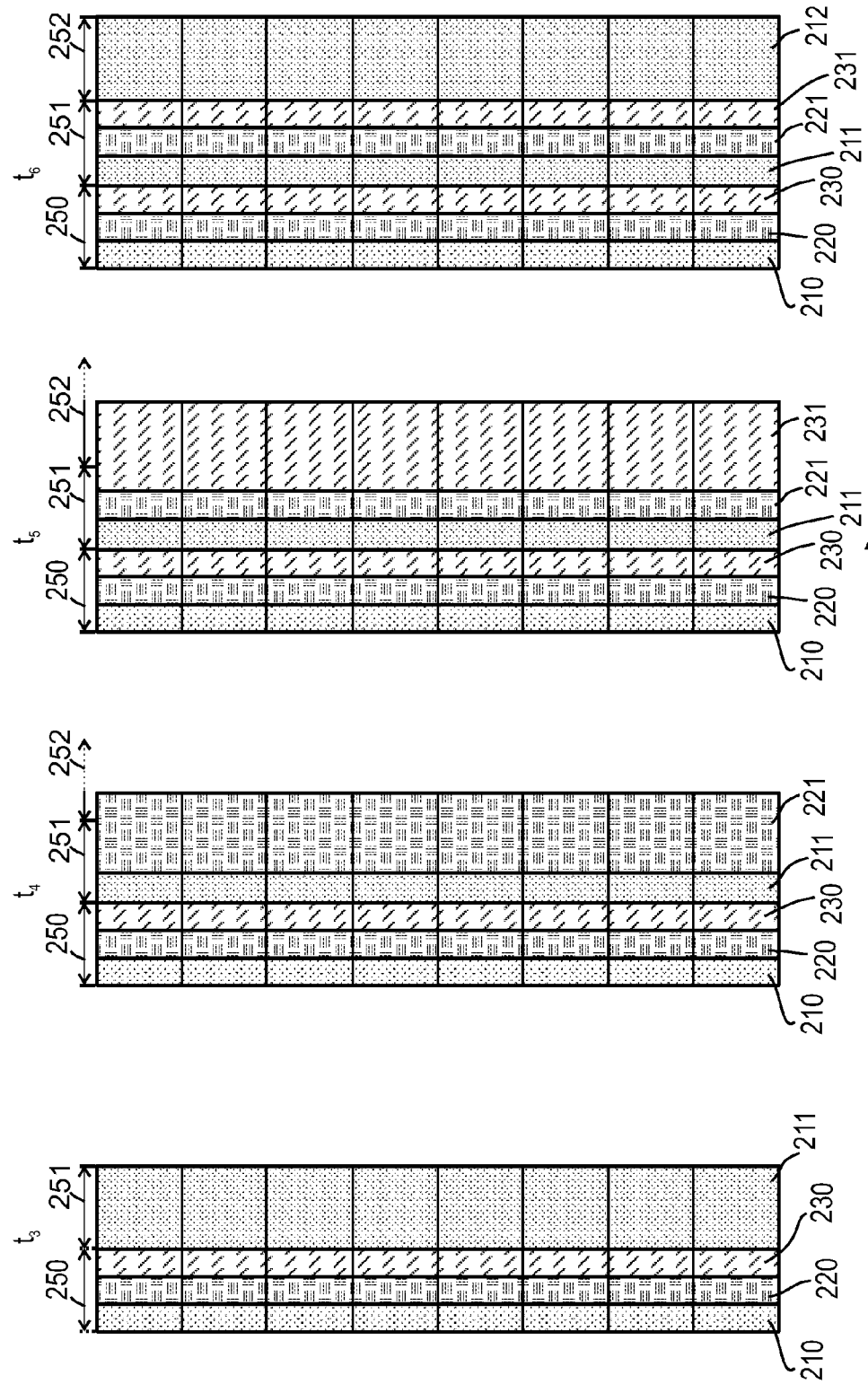

Reference is now made to FIGS. 2A-2B showing two simplified schematic diagram of lines imaged with a line camera using a sequence of three different illumination configurations each shifted by a fraction of a pixel width in accordance with some embodiments of the present invention. FIG. 2A shows a simplified schematic diagram of a first sequence of images captured with three different illumination configurations and FIG. 2B shows a simplified schematic diagram of a second sequence of images captured with three different illumination configurations. According to some embodiments of the present invention, at a time slot $t_0$ a line camera captures exposed pixels 210a-210h forming an exposure area of a plurality of pixels 210, e.g. a plurality of pixels forming a line, using a first illumination configuration. Typically, exposure area 210 spans a first width 250 of a panel being scanned. In some exemplary embodiments, the panel subsequently shifts relative to the line camera along a scanning direction 150 by a fraction of a pixel width, e.g. one third of a pixel width when using a sequence of three illumination configurations. According to some embodiments of the present invention, at a time slot $t_1$ a line camera captures a plurality of pixels, e.g. a plurality of pixels formed in a line, including a second exposure area 220 using a second illumination configuration. This image area includes part of line 210 and part of a next line 211 spanning over a second width 251 of the panel being scanned. Typically, the dimensions of width 250 and width 251 are the same and substantially correspond to a width of a line captured by a line camera. In some exemplary embodiments, each of widths 250 and 251 is narrower than the width of a line captured by a line camera to provide for overlapping between images captured with the same illumination configuration.

The panel subsequently shifts relative to the line camera along scanning direction 150 by a fraction of a pixel width, e.g. one third of a pixel width and at a time slot $t_2$ a line camera captures a plurality of pixels including a third exposure area 230 using a third illumination configuration. This image area includes less of line 210 and more of line 211 (less of width 250 and more of width 251).

The panel subsequently shifts relative to the line camera along scanning direction 150 by a fraction of a pixel width, e.g. one third of a pixel width, so that the entire line of pixels in 211 is captured. According to some embodiments of the present invention, at a time slot $t_3$ exposure area 211 is captured using the first illumination configuration (shown in both FIGS. 2A and 2B for clarity). According to some embodiments of the present invention, capturing of exposure area 211 spans the second width 251 and starts the second sequence of images captured with the three illumination configurations.

According to some embodiments of the present invention, at a time slot $t_4$ a line camera captures a plurality of pixels including a exposure area 221 using the second illumination configuration. According to some embodiments of the present invention, image area 221 spans a portion of width 251 that was not previously covered by exposure area 220 in addition to a part of a width 252.

The panel subsequently shifts relative to the line camera along scanning direction 150 by a fraction of a pixel width, e.g. one third of a pixel width and at a time slot $t_5$ a line camera captures a plurality of pixels including a exposure area 231 using a third illumination configuration. This image area spans more of width 252 and less of width 251.

The panel subsequently shifts relative to the line camera along scanning direction 150 by a fraction of a pixel width, e.g. one third of a pixel width, so that the entire line of pixels in 212 is captured spanning all of width 252. This begins a third sequence. Typically, the dimension of width 252 is the same as that of widths 250 and 251. According to some embodiments of the present invention, the sequence is repeated until an area of the panel to be inspected over one sweep is covered.

According to some embodiments of the present invention, substantially all the images captured with a single illumination configuration are combined to form a continuous image of the panel with each illumination configuration. Although, FIG. 2 shows that one line of pixels is constructed by 8 pixels 210a-210h, it is noted that typically, the number of pixels is several thousands, e.g. 2K-16K pixels.

Typically, the shift error is smaller than the shift itself. According to some embodiments of the present invention, when the shift error between the images captured is smaller than a pixel, or preferably significantly smaller than one pixel; the transformation between the area images taken with different illumination configurations is based on the pre-defined shift between illumination configurations. Thus, according to some embodiments of the present invention, there is no need to calculate the registration separately by analyzing the image data of each of the area images.

Figure 3:
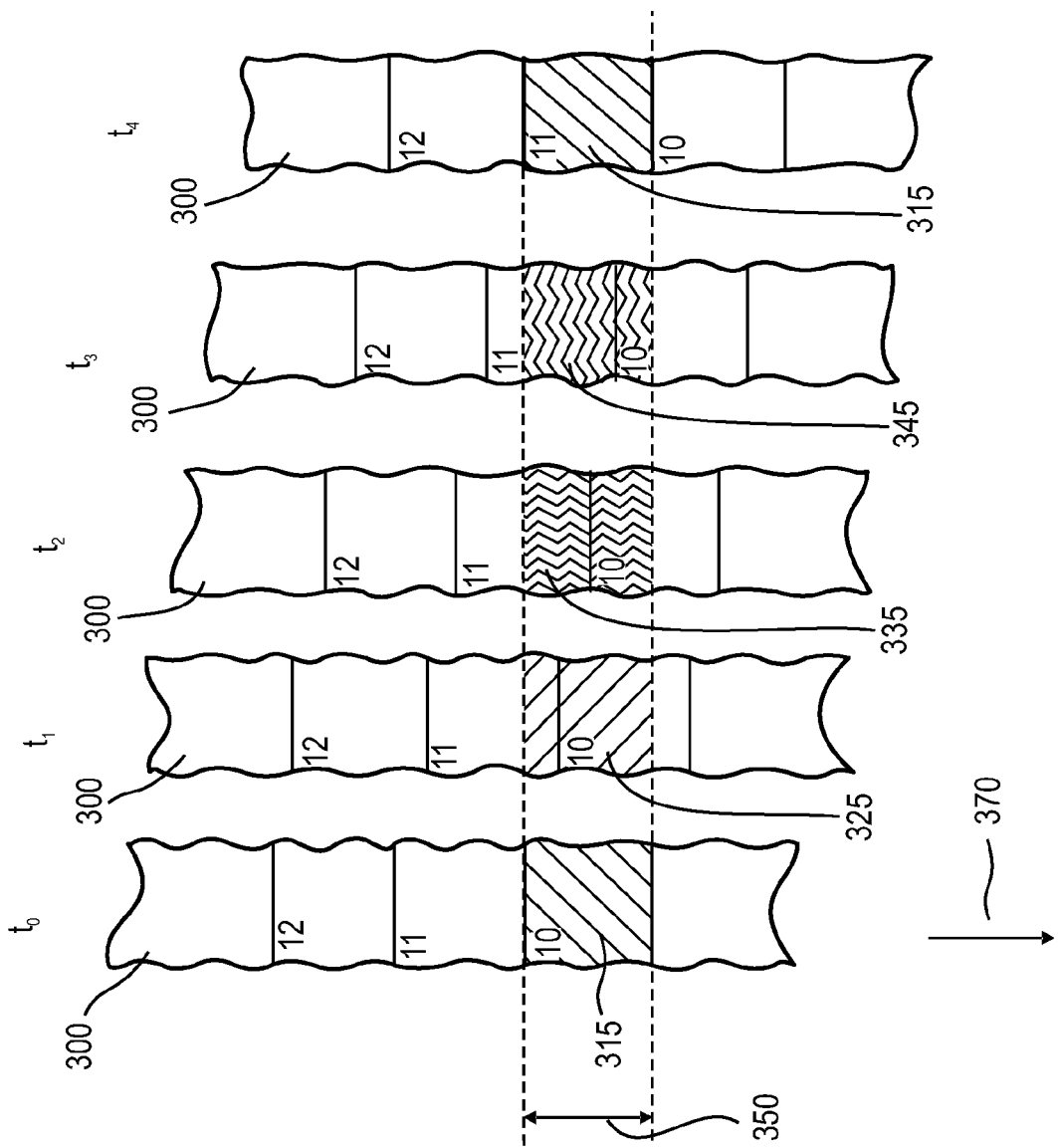
FIG. 3 shows a simplified schematic diagram of a panel moving with respect to an exposure area of a camera during five consecutive capture events in accordance with some embodiments of the present invention.

Reference is now made to FIG. 3 showing a simplified schematic diagram of a panel moving with respect to an exposure area of a camera during five consecutive capture events in accordance with some embodiments of the present invention. According to some embodiments of the present invention, a panel 300 is scanned by advancing the panel in a scanning direction 370 as a stationary imaging unit captures images of portions of panel 300. For clarity, panel 300 is shown as divided into panel areas 10, 11, and 12 where each area corresponds to an area, e.g. a line or a plurality of lines captured by one image. In some exemplary embodiments, panel 300 is wide along a cross-scan direction, e.g. perpendicular to the scan direction, and a plurality of image acquisition devices, e.g. a row of cameras, is used to capture an area including the entire width of the panel to be scanned. In some exemplary embodiments, the full width of panel 300 is scanned over a plurality of sweeps. In some exemplary embodiments, the full width of panel 300 is scanned with a single camera over a single sweep.

According to embodiments of the present invention, at a time slot $t_0$ a portion 315 of panel 300 is illuminated with a first illumination configuration and a portion 315 is captured. In a subsequent time slot $t_1$, panel 300 is shifted and/or offset so a different portion 325 is illuminated. According to some embodiments of the present invention, a second illumination configuration is applied to illuminate portion 325 and a second image is captured. In some exemplary embodiments, portion 325 is offset from portion 315 by a fraction of the length 350 of a single image, e.g. the single image include 1-50 lines of pixels. In some exemplary embodiments, the fraction corresponds to one over the number of different illumination configurations used in a sequence, e.g. repetitive sequence. For example if four illumination configurations are used, the shift between images may be set to ¼ of the length of an image so that the image covers ¾ part of panel area 10 and ¼ part of panel area 11. In some exemplary embodiments, a fraction smaller than one over the number of different illumination configurations, is used so that there is overlap between images taken with the same illumination configuration. Overlap between images taken with the same illumination configuration ensures that there are no gaps in captured areas between contiguous images and may also provide for computing registration between sequential images captured with the same illumination configuration.

In the next time slot $t_2$, panel 300 is shifted in scanning direction 370 so that portion 335 is imaged. In some exemplary embodiments, a third illumination configuration is used for imaging portion 335. For example, imaging portion includes ½ of panel area 10 and ½ of panel area 11. In the next time slot $t_3$, panel 300 is shifted again in scanning direction 370 so that portion 345 is imaged, e.g. ¼ of portion 10 and ¾ of portion 11. In some exemplary embodiments, a forth illumination configuration is used for imaging portion 345. According to some embodiments of the present invention, during the next time slot $t_5$, panel 300 is shifted in scanning direction 370 by a whole image with respect to portion 315, e.g. portion 11, so that portion 355 is imaged with exposure to the first illumination configuration. In such a manner the sequence is repeated until the panel fully scanned. According to embodiments of the present invention, every portion of panel 300 is imaged by each illumination configuration. As such, the images captured may be collated and images from a single illumination configuration may be combined to produce a full image of panel 300 for each illumination configuration.

It is noted that the frequency of switching between illumination configurations is typically higher, e.g. significantly higher, than the mechanical frequency of the system, e.g. the vibration frequency of the system. Typically, the mechanical frequency of the system is up to 100 Hz, e.g. 0-100 Hz, while the frequency of switching between illumination configurations can reach up to 20-40 KHz, e.g. for line cameras. Put in another way, according to some embodiments of the present invention, the spatial shift of the camera with respect to the panel that occurs between image captures from different illumination configurations is at a lower order of magnitude than the tolerance of the system.

Figure 4:
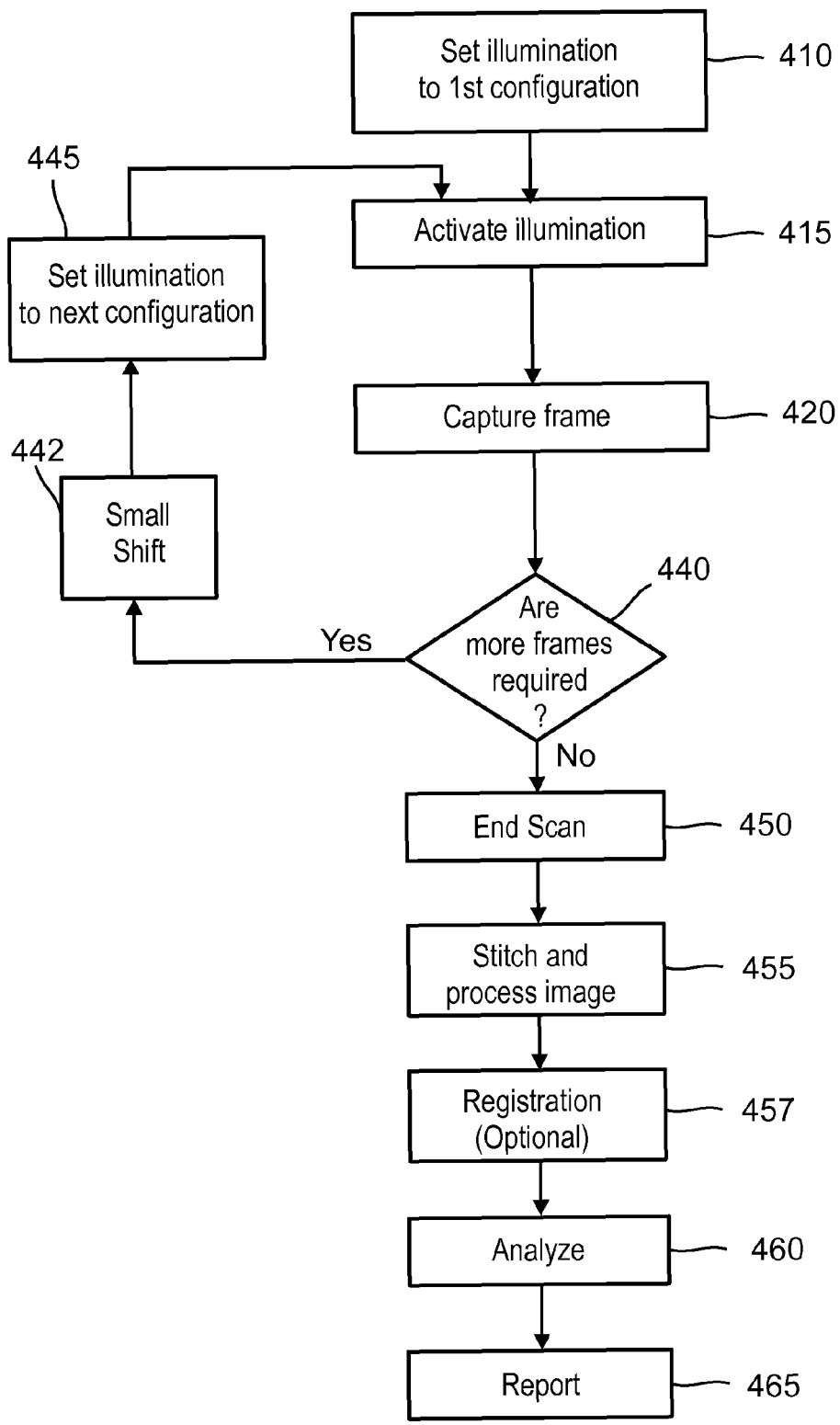
FIG. 4 shows a simplified flow chart of an exemplary method for capturing images of an electrical circuit such as a PCB panel during scanning using a plurality of illumination configurations in accordance with some embodiments of the present invention.

Reference is now made to FIG. 4 showing a simplified flow chart of an exemplary method for capturing images of an electrical circuit such as a PCB panel during scanning using a plurality of illumination configurations in accordance with some embodiments of the present invention. According to some embodiments of the present invention, the illumination source is set to the first illumination configuration in the sequence (block 410). One or more illumination sources may be used to provide the different illumination configuration in the sequence, e.g. more than one illumination source for a single illumination configuration and/or different illumination sources for different illumination configurations. In some exemplary embodiments, a controller controls the switching between the different illumination configurations, e.g. the setting of the required illumination configuration.

According to some embodiments of the present invention, the current illumination configuration is activated (block 415), e.g. flashed and an image line or an image including a plurality of image lines is captured (block 420). In some exemplary embodiments, more than one image is captured. For example during a single illumination period more than one image of single area may be captured, e.g. with more than one flash, and/or different areas may be captured, e.g. different areas over the cross scan direction to cover a wider area of the panel. Typically the image(s) are captured during the illumination period.

A query is made to determine if more images are required (block 440). According to embodiments of the present invention, to continue scanning, the panel advances with respect to the area that the imaging unit exposes (block 442). Typically the advancement (shift) is small, e.g. insignificant, compared to the dimension of an area image inspected. According to some embodiments of the present invention, the shift is less than on pixel. According to some embodiments of the present invention, the shift is between 1-10 pixels and/or between 1-50 pixels. The illumination source(s) is set to a pre-defined subsequent setting (block 445) and at a pre-defined time period corresponding to a pre-defined positioning of the panel with respect to the exposure area, the process, for example the process described in blocks 410-440, is repeated with the new illumination configuration. According to some embodiments of the present invention, at the end of the scanning procedure (block 450), the captured images from each illumination configuration are optionally stitched to create an area image or a full view image (block 455). According to some embodiments of the present invention, each of the area images includes 100-50,000 lines of pixels or more. In some exemplary embodiments, the area images include 10-100 lines. Stitching of images to create an area image or a full view image can be performed by methods known in the art. Optionally, stitching may be performed as part of frame capture process 420 e.g. in a pipelined process, (not shown). According to some embodiments of the present invention, due to the small shift between subsequent images captured as compared to the number of lines included in each area image, registration is not required to align area images captured with the different illumination configurations. According to some embodiments of the present invention, the small shifts provides for automatic registrations between area images constructed with the different illumination configurations of the sequence, e.g. the small shift provides for near perfect alignment. As used herein, automatic registration refers to registration obtained without computation, e.g. without computation to compare image data of the different images. Optionally, registration is computed to align area images captured from the different illumination configurations (block 457). According to some embodiments of the invention registration is computed for images obtained from one of the plurality of illumination configurations. In some exemplary embodiments, registration is performed as the images are being captured, optionally following a query made as to whether this configuration is used for registration to be followed by computation of registration. Optionally, registration may be computed with a time delay or off line, e.g. after all or part, of the images have been captured. Typically, registration is performed on the first illumination configuration in the sequence of illumination configurations. However, it is noted that registration may be performed on images captured from any illumination configuration in the sequence. Typically image processing is performed in parallel to image capture. Optionally, processing may be performed with time delay or off line at the termination of image capturing.

According to some embodiments of the invention, analysis is performed on full view and/or area images, e.g. in order to detect defects in the panel inspected, using methods known in the art (block 460). Typically, analysis is automated. Optionally, a defect report is produced based on the analysis performed (block 465). Optionally, reporting includes displaying the full view and/or area images. Optionally, frame capture, stitching, registration and image analysis may be performed simultaneously or in pipe line mode. Image processing performed may typically include known processing methods used in AOI systems.

Figure 5:
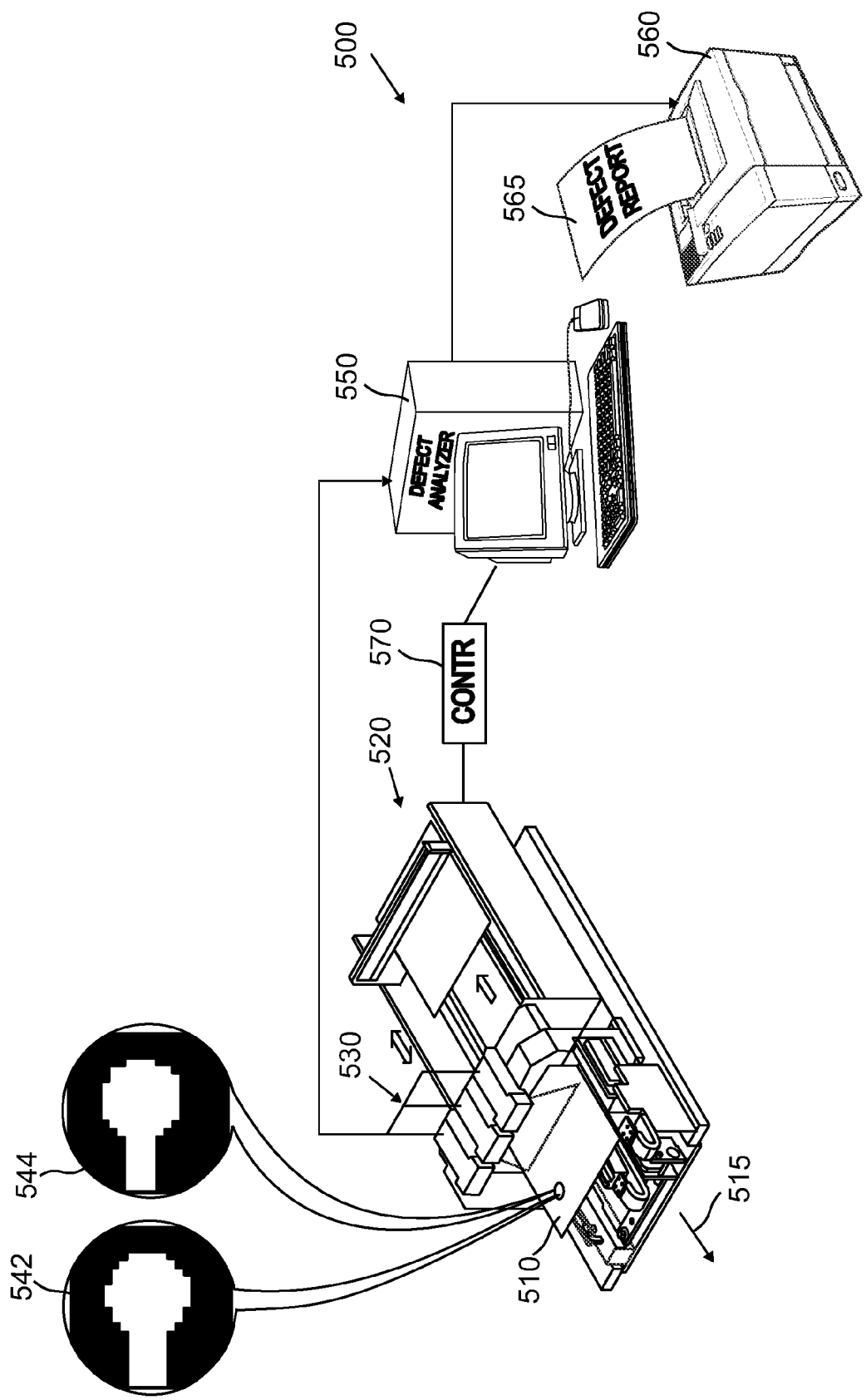
FIG. 5 shows a simplified schematic diagram of an AOI system for inspection of PCB panels in accordance with some embodiments of the present invention.

Reference is now made to FIG. 5 showing a simplified schematic diagram of an AOI system for inspection of PCB panels in accordance with some embodiments of the present invention. According to some embodiments of the present invention an AOI system 500 includes a scanning unit 520, an imaging unit 530, e.g. including one or more imagers and illumination sources, an analyzer 550, typically including one or more processors and memory and at least one output device 560 for reporting output of analyzer 550, e.g. in the form of a defect report 565. Typically scanning unit 520 includes a controller 570 for coordinating movement of a panel with illumination periods and image capture with imaging unit 530. According to embodiments of the present invention, during operation, a panel 510 is inserted into scanning unit 520. Scanning unit 520 advances panel 510 relative to imaging unit 530, e.g. in the scanning direction 515. Images are acquired using different illumination configurations as the panel advances. For exemplary purposes, schematic representations of images taken with two different illumination configurations are shown, e.g. image 542 captured with a first illumination configuration, and image 544 captured with a second illumination configuration. As can be seen in FIG. 5, there is a slight shift in the area covered by image 544 as compared with image 542. As can also be seen, discrepancies between images 542 and 544 captured with different illumination configurations appear due to resolution of the images and/or different properties of the different illuminations. In some exemplary embodiments, imaging unit 530 includes a plurality of imagers, e.g. imagers aligned side by side, and light sources for substantially simultaneously covering an area and/or line of the panel over the full width of the panel. Optionally, registration is calculated between images simultaneously captured with the plurality of imagers. According to some embodiments of the present invention, imaging unit 530 includes a single imager. According to embodiments of the present invention, the acquired images are analyzed by analyzer 550 to obtain a report, e.g. a defect report 565.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A method for scanning a surface with a number of different illumination configurations, the method comprising:
    capturing a plurality of images in a sequential manner during a single sweep, each image including one or more lines of pixels;
    sequentially altering an illumination configuration used to capture the plurality of images according to a predefined sequence of illumination configurations and shifts of the relative position of the imaging unit for capturing each of the plurality of images; and
    repeating the sequence of illumination configurations settings and associated image capture positions until a desired area of the surface is scanned,
    wherein said predefined shift is between 10 pixels and less than one pixel.

2. The method according to claim 1, wherein images captured over one sequence partially overlap.

3. The method according to claim 1, wherein each image covers 100 lines of pixels or less.

4. The method according to claim 1, wherein each image covers 1 line of pixels.

5. The method according to claim 1, wherein the shift of the relative position are provided with a shift error of less than one pixel.

6. The method according to claim 1, comprising acquiring at least two sets of images in a single sweep using at least two different illumination configurations and constructing an area image from each set so as to obtain at least two area images.

7. The method of claim 6, wherein the at least two area images cover a substantially same portion of the surface, wherein the substantially same portion is substantially larger than a portion of the surface covered in a single image.

8. The method according to claim 7, wherein substantially larger is at least 100 times larger.

9. The method according to claim 7, wherein substantially larger is at least 1000 times larger.

10. The method according to claim 6, wherein the at least two area images are automatically registered with an alignment error of less than one pixel.

11. The method according to claim 6, comprising inspecting the area images, wherein the inspecting includes comparing the area images without registering the area images.

12. The method according to claim 6, comprising adjusting spatial alignment between the area images based on the predefined shift.

13. The method according to claim 6, comprising computing registration between one of the area images and a master image and registering the other area image of the at least two area images with the master image using the computed registration.

14. The method according to claim 1, wherein the images are captured with at least one camera selected from a group including: a line camera and a multi-line camera.

15. The method according to claim 1, wherein the illumination configuration is switched on and off or flashed during image capturing.

16. The method according to claim 1, wherein the illumination configurations of the sequence differ in one or more parameters selected from a group including: wavelength, intensity, angle, angular distribution, polarization, and fluorescence.

17. The method according to claim 1, wherein the illumination configuration setting is altered at a frequency greater than the mechanical frequency of a scanning unit scanning the surface.

18. An automatic optical inspection system capable of scanning a surface with a number of different illumination configurations comprising:
    an imaging unit comprising at least one camera and at least one illumination unit, wherein the at least one illumination unit is configured for providing illumination in each of the different illumination configurations and wherein the at least one camera is configured for capturing a series of images over one sweep, each image of the sequence including one or more lines of pixels;
    a scanning unit configured for providing translation between the surface and the imaging unit at a resolution in the order of magnitude of one pixel or less; and
    a controller configured for activating each of the different illumination configurations based on a pre-defined sequence and repeating the sequence for the duration of the sweep and for activating the camera to capture an image during each illumination activation.

19. The system according to claim 18, wherein images captured over the pre-defined sequence partially overlap.

20. The system according to claim 18, wherein the scanning unit is configured for providing translation in the order of magnitude of one pixel or less between capturing of each of the images in the series.

21. The system according to claim 20, wherein the scanning unit provides a translational shift between each image capture that corresponds to a number of pixel lines captured by one image divided by the number of different illumination configurations in the sequence.

22. The system according to claim 18, wherein each image covers 100 lines of pixels or less.

23. The system according to claim 18, wherein each image covers one line of pixels.

24. The system according to claim 18, wherein the error in the translation shift between each image captured corresponds to an error of less than one pixel.

25. The system according to claim 18, wherein the at least one camera is selected from a group including: a line camera and a multi-line camera.

26. The system according to claim 18, wherein the imaging unit comprises a plurality of image sensors aligned side by side to cover a full width of the panel.

27. The system according to claim 18, comprising an analyzer configured for constructing at least two area images from at least two sets of images captured in a single sweep, each set captured with a different illumination configuration.

28. The system of claim 27, wherein the at least two area images cover a substantially same portion of the surface, wherein the substantially same portion is substantially larger than a portion of the surface covered in a single image.

29. The system according to claim 28, wherein substantially larger is at least 100 times larger.

30. The system according to claim 28, wherein substantially larger is at least 1000 times larger.

31. The system according to claim 27, wherein the spatial alignment error between the at least two area images is less than one pixel.

32. The system according to claim 27, wherein the at least two area images are automatically aligned with an alignment error of less than one pixel.

33. The system according to claim 27, wherein the analyzer is configured for comparing the area images without registering the area images.

34. The system according to claim 27, wherein the analyzer is configured for adjusting a spatial alignment between the area images based on a pre-defined translation shift between images captured with the different illumination configuration.

35. The system according to claim 27, wherein the analyzer is configured for computing registration between one of the area images and a master image and for registering another area image from the at least two area images with the master image using the registration computed.

36. The system according to claim 18, wherein the illumination configuration setting is altered at least at a frequency of 1 KHz.

37. The system according to claim 18, wherein the illumination configuration setting is altered at a frequency greater than the mechanical frequency of the automatic optical inspection system.

38. The system according to claim 18, wherein the at least one illumination unit includes at least one LED configured for illuminating a portion of the surface to be imaged.

39. The system according to claim 18, wherein the at least one illumination unit includes illumination with strobe capability.

40. The system according to claim 18, wherein the different illumination configurations differ in one or more parameters selected from a group including: wavelength, intensity, angle, angular distribution, polarization, and fluorescence.

* * * * *